United States Patent [19]

Miyashi et al.

[11] Patent Number: 5,059,742
[45] Date of Patent: Oct. 22, 1991

[54] PROCESS FOR SEPARATING 2,6-DIMETHYLNAPHTHALENE

[75] Inventors: Tsutomu Miyashi, Miyagi; Yoshiro Yamashita, Aichi; Takanori Suzuki, Miyagi; Hiroshi Fujii, Kanagawa, all of Japan

[73] Assignee: Mitsubishi Oil Co., Ltd., Tokyo, Japan

[21] Appl. No.: 365,650

[22] Filed: Jun. 13, 1989

[30] Foreign Application Priority Data

Jun. 13, 1988 [JP] Japan .............................. 63-143773

[51] Int. Cl.$^5$ .............................................. C07C 7/152
[52] U.S. Cl. .................................... 585/860; 585/833; 585/863; 585/865
[58] Field of Search ............... 585/833, 863, 864, 868, 585/865, 860

[56] References Cited

U.S. PATENT DOCUMENTS

| | | | |
|---|---|---|---|
| 3,670,039 | 6/1972 | Davis | 585/817 |
| 3,870,745 | 3/1975 | Angstadt | 585/471 |
| 3,936,509 | 2/1976 | Nagahama et al. | 585/866 X |

OTHER PUBLICATIONS

A. R. Cooper et al, "Gas-Liquid Chromatographic Studies of Electron-Donor-Acceptor Systems", Trans. Faraday Soc. 1967, vol. 63.

*Primary Examiner*—Curtis R. Davis
*Assistant Examiner*—William C. Diemler
*Attorney, Agent, or Firm*—Sughrue, Mion, Zinn, Macpeak & Seas

[57] ABSTRACT

A process for separating 2,6-dimethylnaphthalene form a 2,6-dimethylnaphthalene-containing mixture which comprises mixing said mixture with 2,4,7-trinitro-9-fluorenone to thereby form a complex, separating a solid matter containing said complex and decomposing the solid matter containing the same to thereby separate and collect an oil rich in the 2,6-dimethylnaphthalene. According to this process, 2,6-dimethylnaphthalene can be readily separated at a high selectivity. Further, the 2,4,7-trinitro-9-fluorenone can be readily recovered and reused as such.

7 Claims, No Drawings

PROCESS FOR SEPARATING 2,6-DIMETHYLNAPHTHALENE

FIELD OF THE INVENTION

This invention relates to a process for separating 2,6-dimethylnaphthalene from a mixture containing 2,6-dimethylnaphthalene with the use of 2,4,7-trinitro-9-fluorenone, which will be abbreviated as TNF hereinafter. Dimethylnaphthalene will be abbreviated as DMN hereinafter.

BACKGROUND OF THE INVENTION 2,6-DMN, which may be converted into naphthalene-2,6-dicarboxylic acid by oxidation, has attracted attention as an important material for the production of industrial products such as polyesters or plasticizers. 2,6-DMN is present in a petroleum fraction or a coal tar fraction in the form of a mixture with other DMN isomers. However it is extremely difficult to selectively separate 2,6-DMN from a mixture of DMN isomers by common separation procedures such as distillation, extraction, recrystallization, sublimation or adsorption, since there are ten DMN isomers which are close to each other in physical and chemical properties. Accordingly, there have been proposed some methods for separating 2,6-DMN from a mixture containing the same by forming a complex thereof together with m-nitrobenzoic acid (JP-B-47-29895 and JP-B-47-38440), p-nitrobenzoic acid (JP-B-55-44734) or other nitrobenzene derivatives (JP-B-55-47021) (The term "JP-B" as used herein means an "examined Japanese Patent publication"). However these methods for separating 2,6-DMN by forming a complex thereof are disadvantageous in the selectivity for 2,6-DMN and in the separation and recovery of the same from said complex. Thus none of them has been put into practical use.

SUMMARY OF THE INVENTION

The present inventors attempted to form a complex of 2,6-DMN by using a complexing agent which has never been employed hitherto. As a result, the present inventors found that TNF can readily form a complex together with 2,6-DMN at high selectivity, thus completing the present invention.

Accordingly, the present invention relates to a process for separating 2,6-DMN from a 2,6-DMN-containing mixture which comprises mixing the 2,6-DMN-containing mixture (which will be simply called a mixture hereinafter) with TNF to thereby form a complex of 2,6-DMN and TNF; separating a solid matter containing the formed complex; and decomposing the solid matter containing the complex to thereby separate and collect an oil rich in the 2,6-DMN.

DETAILED DESCRIPTION OF THE INVENTION

The process of the present invention may be applied to any mixture as long as it contains 2,6-DMN and as long as the mixture is free from any component which might inhibit the formation of a 2,6-DMN complex or dissolve the complex. As a complex formation preventing component, a compound such as a nitrogen compound (e.g., acrylonitrile) and a sulfur compound contained in an oil fraction are acknowledged by experimentation. It is preferable to use a hydrocarbon oil which contains various DMN isomers originating from petroleum or coal tar, and more preferably a fraction having a boiling point of about 240° C. to 280° C. which is obtained upon the catalytic cracking or catalytic reforming in refining petroleum. In addition, any other mixtures such as a product increased in the concentration of 2,6-DMN which is obtained by isomerizing a DMN containing mixture decreased in the concentration of 2,6-DMN after separating 2,6-DMN, a product which is obtained by methylating naphthalene or methylnaphthalene, and a product which is obtained by disproportionating methylnaphthalene and the like can be applied to the present invention. As a matter of fact, the concentration of 2,6-DMN in the separated oil would advantageously increase with an increase in the 2,6-DMN content in the starting mixture. It is preferable that the mixture contains about 1% by weight or more, preferably about 5% by weight or more, of 2,6-DMN.

TNF may be generally added to the mixture in such an amount as to give a ratio of the 2,6-DMN to the TNF of about 10/1 by mol or below, preferably about 0.5/1 to 5/1 by mol.

As TNF in the present invention, e.g., the reagent No. T8080-2 (2,4,7-Trinitro-9-fluorenone) disclosed in *Catalog Handbook of Fine Chemicals Aldrich* 1988–1989 is available.

When the mixture is a liquid, it may be contacted with TNF as such. Or when it is a liquid or a solid, it may be dissolved in a light hydrocarbon solvent such as petroleum ether, n-pentane, n-hexane or n-heptane, benzene, toluene or a chlorinated paraffin solvent such as dichloromethane or chloroform to thereby give a solution. To the resulting solution, TNF is added in the form of a powder and the mixture obtained is stirred at about −30° C. to 220° C. The formation of a complex may be appropriately conducted at a temperature of about −30° C. to 150° C., more preferably about 0° C. to 100° C. During this period, stirring may be continued if required.

The formation of the complex requires approximately one minute to 24 hours, depending on the composition of the mixture and/or the conditions under which the complex is to be formed.

The necessary solvent amount is an amount that can dissolve the mixture.

Solid matter containing the complex thus formed may be separated by a conventional solid/liquid separation procedure such as filtration, centrifugation or precipitation. The solid matter may be washed with a light paraffinic hydrocarbon solvent such as petroleum ether, n-pentane, n-hexane or n-heptane, methanol or ethanol to thereby further elevate the purity of the 2,6-DMN.

Next, an oil rich in 2,6-DMN may be collected from the solid matter containing the complex by thermal decomposition or decomposition with other compounds such as esters, ethers, acetonitrile, aromatic hydrocarbons, chlorinated paraffins, alcohols, ketones, or paraffinic hydrocarbons. Among these methods, thermal decomposition is preferable since it can directly recover the separated oil and it enables the reuse of the TNF as such after separating the oil, and it is necessary for decomposition using other compounds to inclulde a collecting step for the separated oil and the complexing agent. The thermal decomposition may be carried out by heating the solid matter to, in general, about 50° C. to 200° C., under a reduced pressure of, in general, about 1 mmHg to 50 mmHg to thereby enable the reuse of the TNF. In the process of the present invention, highly pure TNF, which can be circulated and reused as such, can be regenerated after separating 2,6-DMN from a complex comprising 2,6-DMN and TNF by heating.

It is also possible to further enhance the purity of the 2,6-DMN by repeatedly subjecting the oil thus separated to the formation of a solid matter containing the complex and the decomposition product.

Accordingly, the present invention provides an industrially advantageous process which enables not only ready separating and collecting of 2,6-DMN at high selectivity, compared with conventional methods, but also the reuse of TNF.

To further illustrate the present invention, and not by way of limitation, the following examples will be given.

EXAMPLES 1 AND 2

To each starting oil of the composition as shown in Table 1, which was a fraction obtained at catalytic reforming petroleum oil having a boiling point of 250° C. to 270° C., TNF was added and the resulting mixture was stirred at room temperature for 21 hours. The precipitate thus formed was filtered, washed with n-hexane and dried under 5 mmHg pressure. The solid matter thus obtained, which contained a complex, was thermally decomposed at 115° C. under 14 mmHg pressure and the gas thus evolved was cooled to thereby form a separated oil. Then the oil thus separated was collected. The composition of the starting oil and that of the separated oil were determined by gas chromatography. The residual yellow crystals were identified as TNF by elemental analysis, infrared analysis and melting point. Table 1 shows the results.

TABLE 1

|  | Starting Oil | Ex.1 | Ex.2 | Ex.3 | Ex.4 | Comp. Ex.1 |
| --- | --- | --- | --- | --- | --- | --- |
| Used: | | | | | | |
| Starting Oil (g) | — | 10.14 | 3.00 | 2.41 | 216 mg | — |
| TNF (mg) | — | 600 | 120 | 145 | 136 | — |
| Yield: | | | | | | |
| Complex (mg) | — | 777 | 143 | 188 | 202 | — |
| Separated Oil (mg) | — | 258 | 47 | 62 | 67 | — |
| Composition (wt. %) of oil: | | | | | | |
| Methyl-naphthalene | 8.8 | 1.0 | 0.8 | 0.8 | 0.1 | 24.2 |
| Ethyl-naphthalene | 7.9 | 0.1 | 0.3 | 0.2 | 0.0 | 0.4 |
| 2,6-DMN | 9.7 | 88.9 | 90.2 | 89.2 | 99.1 | 45.3 |
| 2,7-DMN | 9.4 | 5.4 | 4.7 | 5.1 | 0.5 | 5.9 |
| Other DMN isomers | 46.3 | 3.9 | 3.5 | 3.8 | 0.3 | 7.0 |
| Biphenyl etc. | 17.9 | 0.7 | 0.5 | 0.9 | 0.0 | 17.2 |

EXAMPLE 3

By using the TNF collected in Example 1, a separated oil was collected in the same manner as the one described in Example 1. The residual yellow crystals were identified as TNF by elemental analysis, infrared analysis and melting point. Table 1 shows the results.

EXAMPLE 4

The separated oil obtained in Example 1 was dissolved in 1.0 g of dichloromethane and TNF was added thereto. The resulting mixture was stirred at room temperature for five hours. Then the procedure of Example 1 was followed to thereby collect a separated oil. The residual yellow crystals were identified as TNF by elemental analysis, infrared analysis and melting point. Table 1 shows the results.

COMPARATIVE EXAMPLE 1

To 20.0 g of the same starting oil as the one used in Example 1, 5.0 g of m-nitrobenzoic acid was added and the resulting mixture was heated to 100° C. for 15 minutes. After allowing the mixture to cool, the precipitate thus formed was filtered and washed with petroleum ether to thereby collect solid matter containing a complex. This solid matter was dissolved in ethyl ether and washed with 5% caustic soda several times and then with water. After distilling off the ether, 340 mg of a solid was collected. Table 1 shows the composition of this solid determined by gas chromatography.

EXAMPLE 5

A solid matter (raw solid) containing the complex which is obtained by the same manner as in Example 1 using TNF was mixed with each of the compounds for the complex decomposition shown in Table 2 at 20° C. for one hour under stirring. The residual solid was filtered, washed with n-hexane, and dried under 5 mmHg pressure. The amounts of TNF contained in the dried raw solid and the dried residual solid were determined to obtain the decomposition rate of the complex. The results are shown in Table 2.

The decomposition rate is a value which is obtained by subtracting a ratio of (the complexing agent which forms the complex of the residual solid) to (the complexing agent which forms the complex of the raw solid) from 1 and multiplying it by 100.

TABLE 2

| Compound | Amount (g) | Raw solid (mg) | Residual solid (mg) | Complex decomposition rate (%) |
| --- | --- | --- | --- | --- |
| Ethyl acetate | 2.26 | 102.5 | 15.3 | 84 |
| Acetonitrile | 3.15 | 106.0 | 18.9 | 80 |
| Toluene | 2.17 | 182.5 | 34.1 | 78 |
| Methylene chloride | 1.33 | 198.0 | 46.1 | 73 |
| Diethyl ether | 3.51 | 102.5 | 67.5 | 58 |
| Methanol | 7.92 | 104.5 | 38.7 | 68 |
| n-Hexane | 8.25 | 72.0 | 48.4 | 59 |

Accordingly, the process of the present invention for collecting an oil rich in 2,6-DMN from a mixture containing the same which comprises contacting the mixture with TNF and collecting the 2,6-DMN from a solid matter containing the complex thus formed is easily operated and is excellent in selectivity for 2,6-DMN and in separation selectivity (efficiency) of the same from the complex. Namely, a complex of 2,6-DMN with TNF can be formed at a high selectivity by simply mixing the 2,6-DMN-containing mixture with TNF and stirring. When the mixture is a liquid, the complex may be formed by mixing it as such with TNF. When the mixture is a solid, it may be dissolved in a solvent first and then form a complex. The subsequent procedure may be conducted by, for example, a known simple solid/liquid separation method. Then the 2,6-DMN may be collected from the complex thus separated at a high purity by a simple treatment such as heating under reduced pressure. The process of the present invention is further advantageous in that, for example, the TNF which is regenerated simultaneously with the collection of the product may be repeatedly reused as such.

While the invention has been described in detail and with reference to specific embodiments thereof, it will be apparent to one skilled in the art that various changes and modifications can be made therein without departing from the spirit and scope thereof.

What is claimed is:

1. A process for separating 2,6-dimethylnapthalene from a 2,6-dimethylnapthalene-containing mixture, which process comprises mixing said 2,6-dimethylnaphthalene-containing mixture with 2,4,7-trinitro-9-fluorenone to thereby form a complex of 2,6-dimethylnapthalene and 2,4,7-trinitro-9-fluorenone, wherein said mixing of said 2,6-dimethylnaphthalene-containing mixture with said 2,4,7-trinitro-9-fluorenone is carried out at a temperature of 0° C. to 100° C.; separating a solid matter containing the complex of 2,6-dimethylnaphthalene and 2,4,7-trinitro-9-fluorenone thus formed; and decomposing said solid matter containing the complex by heating said solid matter containing the complex to 50° C. to 200° C. under reduced pressure of 1 mm Hg to 50 mm Hg to thereby separate and collect an oil rich in the 2,6-dimethylnaphthalene and separate and collect the 2,4,7-trinitro-9-fluorenone which is then recirculated and reused to form the complex, wherein said 2,4,7-trinitro-9-fluorenone is added in an amount to give a ratio of 2,6-dimethylnaphthalene to 2,4,7-trinitro-9-fluorenone of about 10/1 by mol or below.

2. A process for separating 2,6-dimethylnaphthalene as set forth in claim 1, wherein said 2,6-dimethylnaphthalene-containing mixture is a hydrocarbon oil.

3. A process for separating 2,6-dimethylnaphthalene as set forth in claim 1, wherein said 2,6-dimethylnaphthalene-containing mixture is a fraction having a boiling point of 240° C. to 280° C. of a catalytically reformed petroleum oil or a catalytically cracked petroleum oil.

4. A process for separating 2,6-dimethylnaphthalene as set forth in claim 1, wherein said 2,6-dimethylnaphthalene-containing mixture is dissolved in a light hydrocarbon solvent or a chlorinated paraffin solvent to thereby give a solution, prior to mixing the same with said 2,4,7-trinitro-9-fluorenone.

5. A process for separating 2,6-dimethylnapthalene as set forth in claim 1, wherein said mixture contains about 1% by weight or more of 2,6-dimethylnapthalene.

6. A process for separating 2,6-dimethylnapthalene as set forth in claim 1, wherein said mixture contains about 5% by weight or more of 2,6-dimethylnapthalene.

7. A process for separating 2,6-dimethylnapthalene as set forth in claim 1, wherein said 2,4,7-trinitro-9-fluorenone is added in an amount to give a ratio of 2,6-dimethylnapthalene to 2,4,7-trinitro-9-fluorenone of about 0.5/1 to 5/1 by mol.

* * * * *